United States Patent [19]

Diehr et al.

[11] Patent Number: 4,741,759
[45] Date of Patent: * May 3, 1988

[54] OXYGUANIDINE DERIVATIVES

[75] Inventors: Hans-Joachim Diehr; Christa Fest, both of Wuppertal; Rolf Kirsten, Monheim; Joachim Kluth, Langenfeld; Klaus-Helmut Müller, Duesseldorf; Theodor Pfister, Monheim; Uwe Priesnitz, Solingen; Hans-Jochem Riebel, Wuppertal; Wolfgang Roy, Langenfeld; Ludwig Eue, Leverkusen; Hans-Joachim Santel, Cologne; Robert R. Schmidt, Bergisch-Gladbach, all of Fed. Rep. of Germany

[73] Assignee: Bayer Aktiengesellschaft, Leverkusen, Fed. Rep. of Germany

[*] Notice: The portion of the term of this patent subsequent to Jul. 29, 2003 has been disclaimed.

[21] Appl. No.: 769,187

[22] Filed: Aug. 23, 1985

[30] Foreign Application Priority Data

Aug. 30, 1984 [DE] Fed. Rep. of Germany ....... 3431913

[51] Int. Cl.$^4$ .................... C07D 239/69; A01N 43/54
[52] U.S. Cl. ......................................... 71/92; 544/332
[58] Field of Search ............................ 544/332; 71/92

[56] References Cited

U.S. PATENT DOCUMENTS 4,602,938 7/1986 Moriya et al. ..................... 544/332
4,689,070 8/1987 Shapiro ................................ 71/90

FOREIGN PATENT DOCUMENTS 0117014 8/1984 European Pat. Off. .
0136455 4/1985 European Pat. Off. .
0148498 7/1985 European Pat. Off. .
1089210 6/1959 Fed. Rep. of Germany .
0084530 9/1971 German Democratic Rep. .

Primary Examiner—John M. Ford
Attorney, Agent, or Firm—Sprung Horn Kramer & Woods

[57] ABSTRACT

Herbicidally active oxyguanidine derivatives of the formula

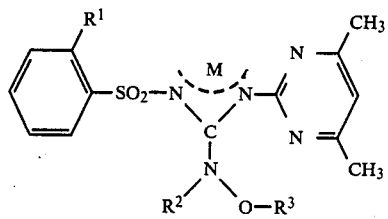

in which
M represents hydrogen or one equivalent of a metal,
$R^1$ represents halogen, $C_1$-$C_4$-alkyl, $C_1$-$C_2$-halogenoalkyl, $C_1$-$C_4$-alkoxy, phenyl or $C_1$-$C_2$-alkoxy-carbonyl,
$R^2$ represents hydrogen or the radical

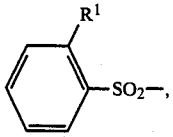

and
$R^3$ represents $C_4$-$C_{12}$-alkyl, isopropyl or—if M represents one equivalent of a metal—also propyl, or represents $C_2$-$C_{12}$-halogenoalkyl, $C_1$-$C_4$-alkoxycarbonyl-$C_1$-$C_2$-alkyl, aminocarbonylmethyl, $C_1$-$C_4$-alkylaminocarbonylmethyl, di-$C_1$-$C_4$-alkylaminocarbonylmethyl, $C_3$-$C_{12}$-alkenyl, $C_3$-$C_{12}$-alkinyl, benzyl which is substituted by halogen, nitro, cyano, $C_1$-$C_4$-alkyl, $C_1$-$C_4$-alkoxy or $C_1$-$C_4$-alkoxycarbonyl, or phenyl, benzhydryl, or phenethyl, all optionally substituted by halogen, nitro, cyano, $C_1$-$C_4$-alkyl, $C_1$-$C_4$-alkoxy or $C_1$-$C_4$-alkoxycarbonyl, or carboxy-$C_1$-$Ca_2$-alkyl, or adducts thereof with strong acids.

15 Claims, No Drawings

OXYGUANIDINE DERIVATIVES

The invention relates to new oxyguanidine derivatives, several processes and new intermediates for their preparation and their use as herbicides.

Various guanidine derivatives have been disclosed as potential herbicides in patent specifications (compare DE-AS (German Published Specification) No. 1,089,210 and East German Patent Specification Nos. 71,016 and 84,530), but they have not hitherto achieved relatively great importance as agents for combating weeds and/or regulating plant growth.

Further guanidine derivatives are the subject of U.S. Pat. No. 4,602,938.

New oxyguanidine derivatives of the general formula (I)

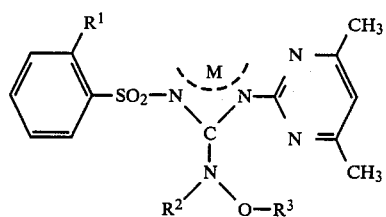

in which

M represents hydrogen or one equivalent of a metal, $R^1$ represents halogen, $C_1$–$C_4$-alkyl, $C_1$–$C_2$-halogenalkyl, $C_1$–$C_4$-alkoxy, phenyl or $C_1$–$C_2$-alkoxy-carbonyl, $R^2$ represents hydrogen or the radical

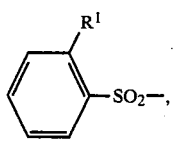

wherein $R^1$ has the abovementioned meaning, and $R^3$ represents $C_4$–$C_{12}$-alkyl, isopropyl or—if M represents one equivalent of a metal—also propyl, or represents $C_2$–$C_{12}$-halogenoalkyl, $C_1$–$C_4$-alkoxycarbonyl-$C_1$–$C_2$-alkyl, aminocarbonylmethyl, $C_1$–$C_4$-alkylaminocarbonylmethyl, di-$C_1$–$C_4$-alkylaminocarbonylmethyl, $C_3$–$C_{12}$-alkenyl, $C_3$–$C_{12}$-alkinyl, benzyl which is substituted by halogen, nitro, cyano, $C_1$–$C_4$-alkyl, $C_1$–$C_4$-alkoxy or $C_1$–$C_4$-alkoxycarbonyl, or phenyl, benzhydryl or phenethyl, all three optionally substituted by halogen, nitro, cyano, $C_1$–$C_4$-alkyl-, $C_1$–$C_4$-alkoxy or $C_1$–$C_4$-alkoxycarbonyl, or carboxy-$C_1$–$C_2$-alkyl, and 1:1 adducts of compounds of the formula (I) with strong acids, have now been found.

If M represents hydrogen, the general formula (I) represents the individual tautomers of the formulae (IA) and (IB)

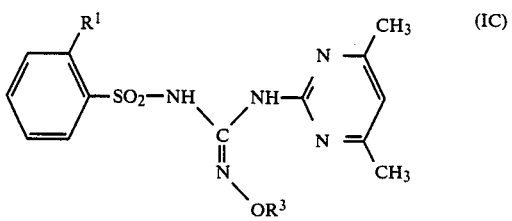

in which $R^1$, $R^2$ and $R^3$ have the abovementioned meanings, and mixtures of the tautomers (IA) and (IB).

The ratio of (IA)/(IB) in the mixture depends on factors which determine the state of aggregation, such as, for example, the temperature, solvent and concentration.

In the case where, in addition to M, $R^2$ also represents hydrogen, another tautomeric form (IC) is possible:

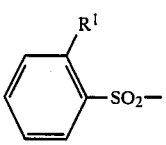

All these tautomers are claimed in the context of the present invention.

The new oxyguanidine derivatives of the formula (I) are obtained by a process in which (a) in the case where $R^2$ represents the radical

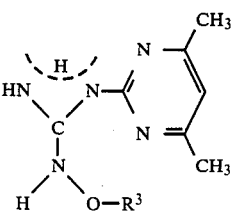

and M represents hydrogen, 4,6-dimethyl-2-oxyguanidino-pyrimidine derivatives of the formula (II)

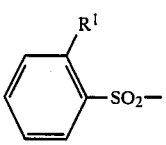

in which $R^3$ has the abovementioned meaning, are reacted with at least two molar equivalents of arenesulphonic acid chlorides of the formula (III)

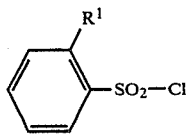
(III)

in which
$R^1$ has the abovementioned meaning, in the presence of acid acceptors and if appropriate in the presence of diluents; or (b) in the case where $R^2$ represents hydrogen, the oxyguanidine derivatives obtainable by the process described under (a), of the formula (ID)

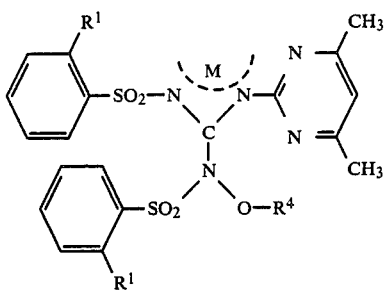
(ID)

in which
M and $R^1$ have the abovementioned meanings and
$R^4$ can have the meaning given above for $R^3$ or represents methyl or ethyl,
are reacted with hydroxylamine derivatives of the formula (IV)

$$H_2N-O-R^3 \quad (IV)$$

in which
$R^3$ has the abovementioned meaning, or with hydrochlorides of compounds of the formula (IV), if appropriate in the presence of acid acceptors and if appropriate in the presence of diluents; or (c) in the case where M represents one equivalent of a metal, the compounds obtainable by the processes described above under (a) and (b), of the formula (I), in which M represents hydrogen and $R^1$, $R^2$ and $R^3$ have the abovementioned meanings, are reacted with metal hydroxides, hydrides or alkanolates or with organometallic compounds, if appropriate in the presence of diluents; or (d) in the case where 1:1 adducts of compounds of the formula (I) with strong acids are to be prepared, oxyguanidine derivatives of the formula (I) in which M represents hydrogen and $R^1$, $R^2$ and $R^3$ have the abovementioned meanings, are reacted with strong acids, if appropriate in the presence of inert diluents.

The new oxyguanidine derivatives of the formula (I) and their 1:1 adducts with strong acids are distinguished by a powerful herbicidal activity.

Surprisingly, the new oxyguanidine derivatives of the formula (I) and their 1:1 adducts exhibit a considerably better herbicidal activity than the guanidines of the same type of action which are already known.

The invention preferably relates to compounds of the formula (I)

in which
M represents hydrogen or one equivalent of sodium, potassium or calcium,
$R^1$ represents fluorine, chlorine, bromine, methyl, chloromethyl, trifluoromethyl, methoxy, phenyl or methoxycarbonyl or ethoxycarbonyl,
$R^2$ represents hydrogen or the radical

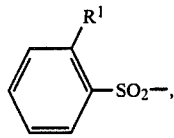

wherein
$R^1$ represents fluorine, chlorine, bromine, methyl, chloromethyl, trifluoromethyl, methoxy, phenyl or methoxycarbonyl or ethoxycarbonyl, and
$R^3$ represents $C_4$-$C_8$-alkyl, isopropyl or—in the case where M represents one equivalent of a metal—also propyl, or represents $C_2$-$C_8$-halogenoalkyl, $C_1$-$C_2$-alkoxycarbonyl-$C_1$-$C_2$-alkyl, aminocarbonylmethyl, $C_1$-$C_3$-alkylaminocarbonylmethyl, di-$C_1$-$C_3$-alkylaminocarbonylmethyl, $C_3$-$C_8$-alkenyl, $C_3$-$C_8$-alkinyl, benzyl which is substituted by fluorine, chlorine, nitro, cyano, methyl, methoxy or $C_1$-$C_2$-alkoxy-carbonyl, or phenyl, benzhydryl, or phenethyl, all three optionally substituted by fluorine, chlorine, nitro, cyano, methyl, methoxy or $C_1$-$C_2$-alkoxycarbonyl.

The invention furthermore preferably relates to 1:1 adducts of the compounds of the formula (I)—as defined above—with hydrogen halide acids, such as hydrogen fluoride, chloride, bromide or iodide, with sulphuric acid or trifluoroacetic acid, with alkanesulphonic acids which have up to 4 carbon atoms and are optionally substituted by fluorine or chlorine, or with benzene- or naphthalene-sulphonic acids, which are optionally substituted by fluorine, chlorine, bromine or methyl.

The invention particularly relates to compounds of the formula (I)
in which
M represents hydrogen or one equivalent of sodium, potassium or calcium,
$R^1$ represents fluorine, chlorine, bromine, chloromethyl or methoxycarbonyl,
$R^2$ represents the radical

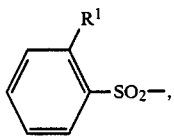

wherein
$R^1$ represents fluorine, chlorine, bromine, chloromethyl or methoxycarbonyl, and
$R^3$ represents $C_4$-$C_8$-alkyl, isopropyl or—in the case where M represents one equivalent of a metal—also propyl, or $C_2$-$C_4$-halogenoalkyl, $C_1$-$C_2$-alkoxycarbonyl-$C_1$-$C_2$-alkyl, aminocarbonylmethyl, $C_3$-$C_5$-alkenyl, $C_3$-$C_5$-alkinyl, benzyl which is substituted by fluorine, chlorine, nitro, methyl or $C_1$-$C_2$-alkoxycarbonyl, or phenyl or phenethyl, optionally substituted by fluorine, chlorine, nitro, methyl or $C_1$-$C_2$-alkoxycarbonyl, and—in the case where M represents hydrogen—the 1:1 adducts of compounds of the formula (I) defined above with hydrochloric acid, sulphuric acid, trifluoroacetic acid, methanesulphonic acid, benzenesulphonic acid and p-toluenesulphonic acid.

If, for example, 2-fluoro-benzenesulphonyl chloride and N'-(4,6-dimethylpyrimidin-2-yl)-N''-isopropoxyguanidine are used as starting substances for process variant (a), the course of the reaction can be outlined by the following equation:

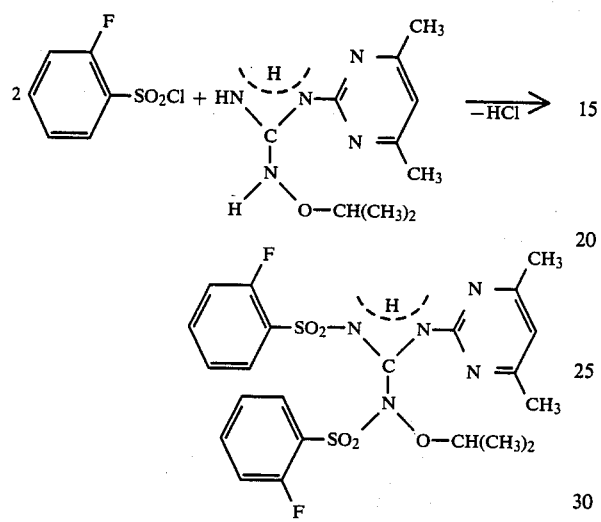

If, for example, N'-(4,6-dimethyl-pyrimidin-2-yl)-N''-methoxy-N'',N'''-bis-(2-bromo-benzenesulphonyl)-guanidine and O-hexylhydroxylamine are used as starting substances for process variant (b), the course of the reaction can be outlined by the following equation:

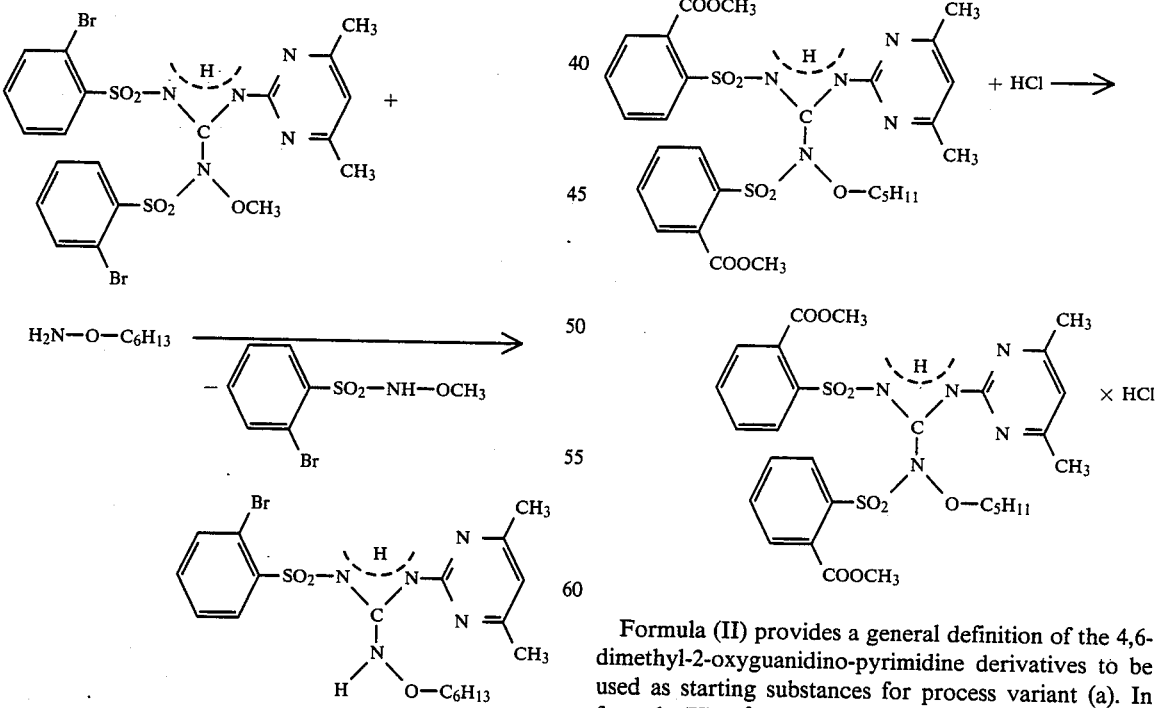

If, for example, N'-(4,6-dimethyl-pyrimidin-2-yl)-N''-phenoxy-N'''-(2-chloro-benzenesulphonyl)-guanidine and potassium ethanolate are used as starting substances for process variant (c), the course of the reaction can be outlined by the following equation:

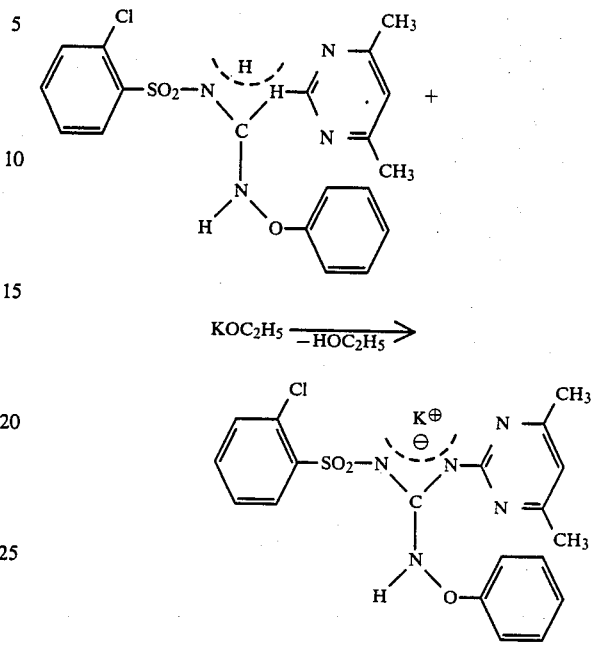

If, for example, N'-(4,6-dimethyl-pyrimidin-2-yl)-N''-pentoxy-N'',N'''-bis-(2-methoxycarbonylbenzenesulphonyl)-guanidine and hydrochloric acid are used as starting substances for process variant (d), the course of the reaction can be outlined by the following equation:

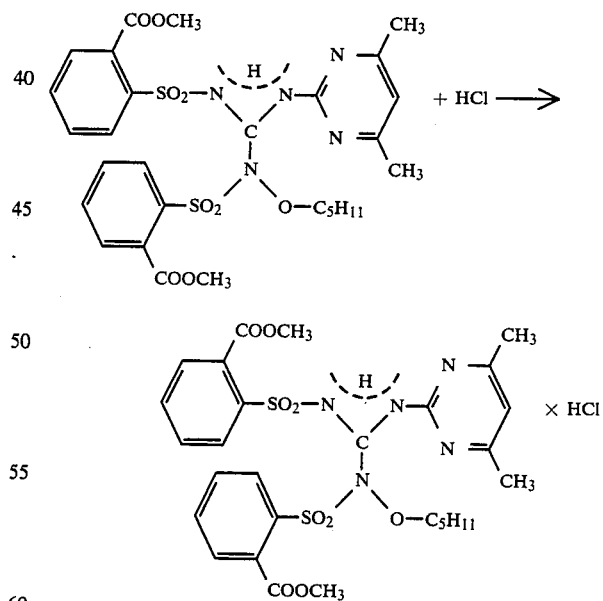

Formula (II) provides a general definition of the 4,6-dimethyl-2-oxyguanidino-pyrimidine derivatives to be used as starting substances for process variant (a). In formula (II), $R^3$ preferably or in particular has the same meaning as has been given above as preferred or particularly preferred in the context of the definition of the substituents of formula (I).

Examples of starting substances of the formula (II) which may be mentioned are: N'-(4,6-dimethyl-pyrimidin-2-yl)-N''-propoxy-guanidine, -N''-isopropoxy-guanidine, -N''-butoxy-guanidine, -N''-isobutoxy-guanidine, -N''-sec.-butoxy-guanidine, -N''-pentoxy-guanidine, -N''-isopentoxy-guanidine, -N''-sec.-pentoxy-guanidine, -N''-hexyloxy-guanidine, -N''-isohexyloxy-guanidine, -N''-heptyloxy-guanidine, -N''-isoheptyloxy-guanidine, -N''-ocytyloxy-guanidine, -N''-isooctyloxy-guanidine, -N''-allyloxy-guanidine, -N''-crotyloxy-guanidine, -N''-(2-chloro-ethoxy)-guanidine, -N''-(2-fluoro-ethoxy)-guanidine, -N''-(2-chloro-propoxy)-guanidine, -N''-(3-chloropropoxy)-guanidine, -N''-(4-chloro-butoxy)-guanidine, -N''-methoxycarbonylmethoxy-guanidine, -N''-ethoxycarbonylmethoxy-guanidine, -N''-(1-methoxycarbonylethoxy)-guanidine, -N''-(1-ethoxy-carbonyl-ethoxy)-guanidine, -N''-aminocarbonylmethoxy-guanidine, -N''-(phenyl-ethoxy)-guanidine, -N''-phenoxy-guanidine, -N''-(4-methyl-benzyloxy)-guanidine, -N''-(4-chloro-benzyloxy)-guanidine, -N''-(4-nitro-benzyloxy)-guanidine, -N''-(2,6-dichloro-benzyloxy)-guanidine, -N''-(4-ethoxy-carbonylbenzyloxy)-guanidine and -N''-(4-methoxycarbonyl-benzyloxy)-guanidine.

The starting substances of the formula (II) are known in some cases (compare J. Chem. Soc. 1962, 3915); some of them are the subject of application Ser. No. 578,345, filed Feb. 9, 1984, now pending, corresponding to DE-OS (German Published Specification) No. 3,334,455.

The new compounds of the formula (IIa)

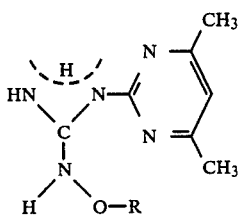

in which

R represents $C_2$–$C_{12}$-halogenoalkyl, $C_1$–$C_4$-alkoxycarbonyl-$C_1$–$C_2$-alkyl, aminocarbonylmethyl, $C_1$–$C_4$-alkylaminocarbonylmethyl, di-$C_1$–$C_4$-alkylaminocarbonylmethyl, $C_4$–$C_{12}$-alkenyl, $C_4$–$C_{12}$-alkinyl, benzyl which is substituted by halogen, nitro, cyano, $C_1$–$C_4$-alkyl, $C_1$–$C_4$-alkoxy or $C_1$–$C_4$-alkoxycarbonyl, or phenyl or phenethyl, optionally substituted by halogen, nitro, cyano, $C_1$–$C_4$-alkyl, $C_1$–$C_4$-alkoxy or $C_1$–$C_4$-alkoxy-carbonyl, are obtained by a process in which 2-cyanoamino-4,6-dimethyl-pyrimidine of the formula (V)

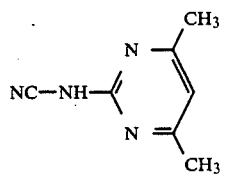

is reacted with hydroxylamine derivatives of the formula (Iva)

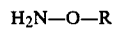   (Iva)

in which

R has the abovementioned meaning, or with hydrochlorides thereof, if appropriate in the presence of diluents, such as, for example, ethanol, isopropanol or butanol, at temperatures between 20° C. and 150° C., preferably between 50° C. and 120° C., and, if appropriate, the reaction products are treated with acid acceptors, such as, for example, ammonia, sodium hydroxide solution or sodium carbonate. The compounds of the formula (II) can also be in the form of various tautomers; the invention also relates to these compounds.

2-Cyanoamino-4,6-dimethyl-pyrimidine of the formula (V) is already known (compare J. Chem. Soc. 1953, 1725).

Hydroxylamine derivatives of the formula (Iva) are likewise already known and can be prepared by processes which are known per se (compare Chem. Pharm. Bull. 15 (1967), 345; Bull. Soc. Chim. France 1958, 664; Synthesis 1976, 682; J. Chem. Soc. 1930, 228 and Helv. Chim. Acta 45 (1962), 1387).

Formula (III) provides a general definition of the arenesulphonic acid chlorides also to be used as starting substances for process variant (a). In formula (III), $R^1$ preferably or particularly has the same meaning as given above as preferred or particularly preferred in the context of the definition of the substituents of formula (I).

Examples of starting substances of the formula (III) which may be mentioned are: 2-chloro-, 2-fluoro-, 2-bromo-, 2-methyl-, 2-trifluoromethyl-, 2-methoxy-, 2-phenyl and 2-methoxycarbonyl-benzenesulphonyl chloride.

The arenesulphonic acid chlorides of the formula (III) are known and can be prepared by processes which are known per se (compare J. Org. Chem. 33 (1968), 2104; J. Org. Chem. 25 (1960), 1824 and DE-OS (German Published Specification) No. 2,308,262).

Formula (ID) provides a general definition of the oxyguanidine derivatives to be used as starting substances for process variant (b). In formula (ID), M and $R^1$ preferably or especially have the same meanings as have been given above as preferred or particularly preferred in the context of the definition of the substituents of formula (I), and $R^4$ preferably represents methyl.

Examples which may be mentioned of the compounds of the formula (ID) to be used as starting substances in process (b) are: N'-(4,6-dimethyl-pyrimidin-2-yl)-N''-methoxy-, -N'',N'''-bis-(2-chloro-benzenesulphonyl)-, -N'',N'''-bis-(2-bromo-benzenesulphonyl)-, -N'',N'''-bis-(2-fluoro-benzenesulphonyl)-, -N'',N'''-bis-(2-methylbenzenesulphonyl)-, -N'',N'''-bis-(2-trifluoromethylbenzenesulphonyl)-, -N'',N'''-bis-(2-methoxy-benzenesulphonyl)-, -N'',N'''-bis-(2-phenyl-benzenesulphonyl)- and -N'',N'''-bis-(2-methoxycarbonyl-benzenesulphonyl)-guanidine.

The guanidine derivatives of the formula (ID) can be prepared by the process described above under (a).

Formula (IV) provides a general definition of the hydroxylamine derivatives also to be used as starting substances in process variant (b). In formula (IV), $R^3$ preferably or especially has the meaning given above as preferred or particularly preferred in the context of the definition of the substituents of formula (I).

Examples of starting substances of the formula (IV) which may be mentioned are: O-propyl-, O-isopropyl-, O-butyl-, O-isobutyl-, O-sec.-butyl-, O-pentyl-, O-isopentyl-, O-sec.-pentyl-, O-hexyl-, O-isohexyl-, O-heptyl-, O-isoheptyl-, O-octyl-, O-isooctyl-, O-allyl-, O-crotyl, O-(2-chloro-ethyl)-, O-(2-fluoro-ethyl)-, O-(2- chloro-propyl)-, O-(3-chloro-propyl)-, O-(4-chloro-butyl)-, O-methoxycarbonylmethyl-, O-ethoxycarbonylmethyl-, O-(1-methoxycarbonyl)-ethyl-, O-(1-ethoxycarbonyl)-ethyl-, O-aminocarbonylmethyl-, O-(2-phenyl-ethyl)-, O-phenyl-, O-(4-methyl-benzyl)-, O-(4-fluoro-benzyl)-, O-(4-chloro-benzyl)-, O-(4-nitro-benzyl)-, O-(2,6-dichloro-benzyl)-, O-(4-methoxycarbonyl-benzyl)-, O-(4-ethoxycarbonylbenzyl) and benzhydryl-hydroxylamine.

Hydroxylamine derivatives of the formula (IV) are known and can be prepared by processes which are known per se (compare Chem. Pharm. Bull. 15 (1967), 345; Bull. Soc. Chim. France 1958, 664; Synthesis 1976, 682; J. Chem. Soc. 1930, 228 and Helv. Chim. Acta 45 (1962), 1387).

Formula (I)—with the proviso that M represents hydrogen—provides a general definition of the oxyguanidine derivatives to be used as starting substances in process variant (c). In formula (I)—where this relates to compounds to be used as starting substances for process (c)—M preferably represents hydrogen and the radicals $R^1$, $R^2$ and $R^3$ preferably or especially have the same meanings as have been given above as preferred or particularly preferred in the context of the definition of the substituents of formula (I).

The compounds of the formula (I) to be used as starting substances for process (c) can be prepared by the processes described under (a) and (b).

Examples which may be mentioned of the metal hydroxides, hydrides or alkanolates or organometallic compounds to be used in process (c) are: the hydroxides of lithium, sodium, potassium, magnesium and calcium, the hydrides of lithium, sodium and calcium, sodium methanolate and ethanolate, potassium methanolate, ethanolate and potassium tert.-butanolate, and butyl-lithium and isopropyl-magnesium chloride.

Formula (I)—with the proviso that M represents hydrogen—provides a general definition of the oxyguanidine derivatives to be used as starting substances in process variant (d). In formula (I)—where this relates to compounds to be used as starting substances for process (d)—M represents hydrogen and the radicals $R^1$, $R^2$ and $R^3$ preferably or especially have the same meanings as have been given above as preferred or particularly preferred in the context of the definition of the substituents of formula (I).

The compounds of the formula (I) to be used as starting substances for process (d) can be prepared by the processes described under (a) and (b).

Strong acids are used as starting substances in process (d). These are preferably hydrogen halide acids, such as hydrogen fluoride, hydrogen chloride, hydrogen bromide and hydrogen iodide, and furthermore sulphuric acid and phosphoric acid, or alkanesulphonic acids which have up to 4 carbon atoms and are optionally substituted by fluorine or chlorine, such as, for example, methanesulphonic acid, ethanesulphonic acid, chloromethanesulphonic acid, 2-chloroethanesulphonic acid and trifluoromethanesulphonic acid, and furthermore benzenesulphonic acid, p-toluenesulphonic acid, naphthalene-1-sulphonic acid, naphthalene-2-sulphonic acid and naphthalene-1,4-, -1,5-, -1,6-, -2,6- and -2,7-disulphonic acid. Hydrochloric acid (hydrogen chloride), sulphuric acid, benzenesulphonic acid and p-toluenesulphonic acid are particularly preferred.

Process (a) according to the invention for the preparation of the new compounds of the formula (I) is preferably carried out using diluents. Possible diluents are virtually all the inert organic solvents, but preferably aprotic polar solvents. These include optionally halogenated hydrocarbons, such as, for example, methylene chloride, chloroform, toluene and chlorobenzene, nitriles, such as, for example, acetonitrile and propionitrile, dimethylformamide, dimethylacetamide, dimethylsulphoxide, sulpholane, hexamethylphosphoric acid triamide, 1,2-dimethoxyethane, pyridine and 2-methyl-5-ethyl-pyridine.

Virtually all the acid-binding agents which can usually be employed can be used as acid acceptors in process (a). These include, in particular, alkali metal hydrides and alkaline earth metal hydrides, organo-metallic compounds, such as butyl-lithium, and furthermore aliphatic, aromatic or heterocyclic amines, such as trimethylamine, triethylamine, N,N-dimethylaniline, N,N-dimethyl-benzylamine, diazabicyclooctane (DABCO), diazabicycloundecene (DBU), pyridine, 2-methyl-5-ethyl-pyridine and 4-dimethylamino-pyridine.

The reaction temperatures can be varied within a substantial range in process (a). In general, the reaction is carried out between $-80°$ C. and $+100°$ C., preferably between $-30°$ C. and $+50°$ C. The process according to the invention is in general carried out under normal pressure.

For carrying out process (a), in general between 2 and 5 moles, preferably between 2.1 and 3 moles, of arenesulphonic acid chloride of the formula (III) are employed per mole of compound of the formula (II). The reaction components are usually brought together at room temperature or with external cooling, and the reaction mixture is stirred until the reaction has ended.

The new compounds are worked up and isolated by customary methods: the mixture is shaken with water and a water-immiscible solvent, such as, for example, methylene chloride, chloroform or toluene, if appropriate after distilling off volatile components, and the organic phase is washed with water, dried, filtered and concentrated. The products of the formula (I), which remain in the residue, are made to crystallize by digestion with organic solvents, such as, for example, diethyl ether, ethyl acetate, ethanol or isopropanol, and, if appropriate, purified by recrystallization.

Process (b) according to the invention is preferably carried out using diluents. Possible diluents are virtually all the inert organic solvents and, if appropriate, in addition also water. These solvents include, in particular, alcohols, such as methanol, ethanol and n- and iso-propanol, ethers, such as tetrahydrofuran, dioxane and 1,2-dimethoxyethane, esters, such as methyl acetate and ethyl acetate, nitriles, such as, for example, acetonitrile or propionitrile, and dimethylformamide and water.

Acid-binding agents which do not have nucleophilic properties which noticeably compete with the hydroxylamine derivatives of the formula (IV) can be used as acid acceptors in process (b).

Such acid-binding agents which may be mentioned are alkali metal and alkaline earth metal carbonates, such as, for example, potassium carbonate and calcium carbonate, tertiary amines, such as, for example, triethylamine, N,N,dimethylaniline and N,N-dimethylbenzylamine, and nitrogen-containing heterocyclic compounds, such as, for example, pyridine, diazabicyclooctane (DABCO) and diazabicycloundecene (DBU).

The reaction temperature can be varied within a substantial range in process (b). In general, the reaction is carried out between 0° C. and 150° C., preferably between 10° C. and 100° C. Process (b) is in general carried out under normal pressure.

For carrying out process (b) according to the invention, in general between 1 and 10 moles, preferably between 2 and 5 moles, of hydroxylamine derivative of the formula (IV) or hydrochloride thereof are employed per mole of the compound of the formula (ID).

In general, the compound of the formula (ID) is taken with the diluent at 20° C. or with gentle cooling, and the hydroxylamine derivative of the formula (IV), or the hydrochloride thereof and a suitable acid acceptor, is added. The reaction mixture is then in general stirred at 20° C. or elevated temperature until the reaction has ended.

Working up can be carried out by customary methods. If the products of the formula (I) are obtained as crystals from the reaction mixture, they can be isolated by filtration with suction. Otherwise, the mixture is diluted with water—if appropriate after being concentrated—and extracted with a solvent which is virtually water—immiscible, such as, for example, methylene chloride. The products of the formula (I) can be obtained in a pure form by washing the extraction solution with water, drying and filtering it, concentrating the filtrate and recrystallising the residue.

Process (c) according to the invention is preferably carried out using diluents. Possible diluents are virtually all the inert organic solvents. These include, in particular, alcohols, such as, for example, ethanol and n- and iso-propanol, ethers, such as, for example, tetrahydrofuran, dioxane and 1,2-dimethoxyethane, esters, such as, for example, methyl acetate and ethyl acetate, and nitriles, such as, for example, acetonitrile.

The reaction temperature can be varied within a substantial range in process (c). In general, the reaction is carried out between −20° C. and +50° C., preferably between 0° C. and 30° C. Process (c) is in general carried out under normal pressure.

For carrying out process (c) according to the invention, in general between 0.9 and 1.2 moles, preferably between 0.95 and 1.1 moles, of metal compound are employed per mole of oxyguanidine derivative of the formula (I).

In general, the oxyguanidine derivatives of the formula (I) and the diluent are taken and the metal compound—if appropriately dissolved in the diluent—is metered in—if necessary with gentle external cooling. The reaction mixture is stirred until the reaction has ended. The salt-like products of the formula (I) are in general obtained as crystals and can be isolated by filtration with suction.

Process (d) according to the invention is preferably carried out using diluents. Possible diluents are virtually all the inert organic solvents. These include, in particular, alcohols, such as methanol, ethanol and n- and iso-propanol, ethers, such as tetrahydrofuran, dioxane and 1,2-dimethoxyethane, esters, such as methyl acetate and ethyl acetate, and ketones, such as acetone, methyl ethyl ketone and methyl isobutyl ketone.

If the acids used as starting substances are employed in aqueous solution, it may also be advantageous to use acetic anhydride as the diluent.

The reaction temperature can be varied within a substantial range in process (d). In general, the reaction is carried out between −20° C. and +50° C., preferably between 0° C. and 30° C. Process (d) is in general carried out under normal pressure.

For carrying out process (d) according to the invention, in general between 1 and 10 moles, preferably between 1 and 5 moles, of a strong acid are employed per mole of oxyguanidine derivative of the formula (I).

In general, the oxyguanidine derivatives of the formula (I) and the diluent are taken and the strong acid is metered in—if necessary with gentle external cooling. The reaction mixture is stirred until the reaction has ended. The 1:1 adducts are in general obtained as crystals and can be isolated by filtration with suction.

The active compounds according to the invention can be used defoliants, desiccants, agents for destroying broad-leaved plants and, especially, as weedkillers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera

Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Laminum, Veronica, Abutilon, Emex, Datura, Viola, Geleopsis, Papaver and Centaurea.

Dicotyledon cultures of the genera

Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera

Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera

Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

The active compounds according to the invention can be used for combating monocotyledon and dicotyledon weeds in monocotyledon and dicotyledon crops by the pre-emergence and post-emergence method.

Control of germinating, emerging and already established weeds in permanent crops is also possible with the active compounds according to the invention, such as total combating of vegetation on non-agricultural land.

The active compounds can be converted to the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene or alkyl naphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silicic acid, alumina and silicates, as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkylsulphonates, alkylsulphates, arylsulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention, as such or in the form of their formulations, can also be used, for combating weeds, as mixtures with known herbicides, finished formulations or tank mixes being possible.

Possible components for the mixtures are known herbicides, such as, for example, N-(2-benzothiazolyl)-N,N'-dimethyl-urea, 3-(3-chloro-4-methylphenyl)-1,1-dimethylurea, 3-(4-isopropylphenyl)-1,1-dimethylurea, 4-amino-6-(1,1-dimethylethyl)-3-methylthio-1,2,4-triazin-5-(4H)-one, 4-amino-6-(1,1-dimethyl-ethyl)-3-ethylthio-1,2,4-triazin-5(4H)-one, 1-amino-6-ethylthio-3-(2,2-dimethylpropyl)-1,3,5-triazin-2,4-(1H,3H)-dione, 4-amino-3-methyl-6-phenyl-1,2,4-triazin-5(4H)-one, 2-chloro-4-ethylamino-6-isopropyl-amino-1,3,5-triazine, the R-enantiomer of trimethylsilyl)-methyl 2[4-(3,5-dichloropyridin-2-oxy)-phenoxy]-propionate, the R-enantiomer of (2-benzyloxy)-ethyl 2-[4-(3,5-dichloropyridyl-2-oxy)-phenoxy]-propionate, 2,4-dichlorophenoxyacetic acid, 2-(2,4-dichlorophenoxy)-propionic acid, 4-chloro-2-methylphenoxy-acetic acid, 2-(2-methyl-4-chloro-phenoxy)-propionic acid, 3,5-diiodo-4-hydroxy-benzonitrile, 3,5-dibromo-4-hydroxy-benzonitrile and diphenyl ethers and phenylpyridazines, such as, for example, pyridates. Surprisingly, some mixtures also show a synergistic action.

Mixtures with other known active compounds, such as fungicides, insecticides, acaricides, nematicides, bird repellents, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants. They can also be incorporated into the soil before sowing. Especially when used by the post-emergence method, the active compounds according to the invention can also be applied in combination with emulsifiable oils, surface-active substances and other additives.

The amount of active compound used can vary within a substantial range. It depends essentially on the nature of the desired effect. In general, the amounts used are between 0.001 and 10 kg of active compound per hectare of soil surface, preferably between 0.01 and 5 kg per ha.

The active compounds according to the invention also exhibit a fungicidal side effect, for example an action against Pyricularia oryzae on rice, and a (systemic) bactericidal activity.

The preparation and use of the active compounds according to the invention can be seen from the following examples.

PREPARATION EXAMPLES

Example 1

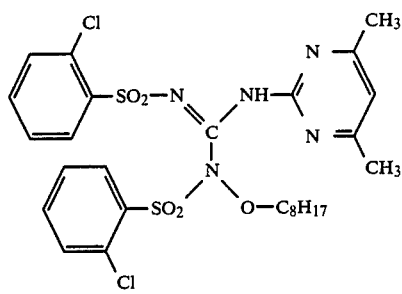

(Process (a))

A mixture of 7.4 g (0.025 mole) of N'-(4,6-dimethyl-pyrimidin-2-yl)-N'''-octyloxy-guanidine, 10.7 g (0.051 mole) of 2-chloro-benzenesulphonyl chloride and 30 ml of pyridine is stirred at 20° C. for 15 hours. After most of the pyridine has been distilled off under a waterpump vacuum, the residue is made to crystallize by digestion with ethanol and the product is isolated by filtration with suction.

7.7 g (48% of theory) of N'-(4,6-dimethylpyrimidin-2-yl)-N''-octyloxy-N''',N''''-bis-(2-chlorobenzenesulphonyl)-guanidine of melting point 120° C. are obtained.

Example 2

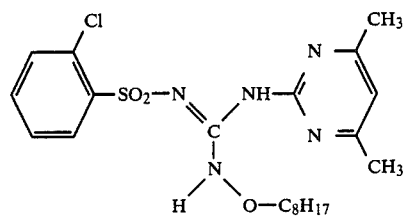

(Process (b))

A mixture of 13.8 g (0.025 mole) of N'-(4,6-dimethyl-pyrimidin-2-yl)-N''-methoxy-N''',N''''-bis-(2-chlorobenzenesulphonyl)-guanidine, 3.7 g (0.026 mole) of O-octylhydroxylamine and 80 ml of ethanol is heated at the boiling point under reflux for 15 hours. The mixture is then concentrated under a waterpump vacuum and the product is made to crystallize by trituration and is isolated by filtration with suction. 3.2 g (27% of theory) of N'-(4,6-dimethylpyrimidin-2-yl)-N''-octyloxy-N''''-(2-chloro-benzenesulphonyl)-guanidine of melting point 55° C. are obtained.

Example 3

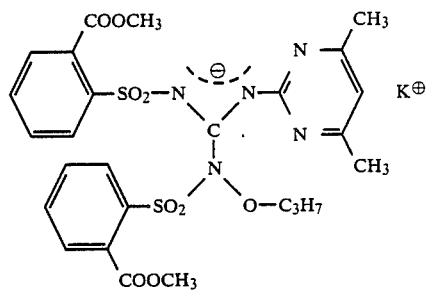

(Process (c))

A mixture of 6.2 g (0.01 mole) of N'-(4,6-dimethyl-pyrimidin-2-yl)-N''-propoxy-N''',N''''-bis-(2-methoxy-carbonyl-benzenesulphonyl)-guanidine, 0.9 g (0.011 mole) of potassium ethanolate and 20 ml of ethanol is stirred at 20° C. for 15 hours. The product obtained as crystals is then isolated by filtration with suction.

5.4 g (82% of theory) of N'-(4,6-dimethylpyrimidin-2-yl)-N''-propoxy-N''',N''''-bis-(2-methoxy-carbonylbenzenesulphonyl)-guanidine potassium salt of melting point 149° C. are obtained.

Example 4

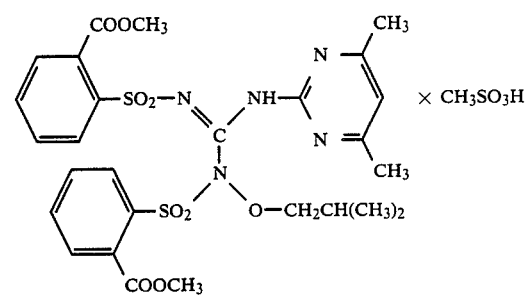

(Process (d))

A mixture of 6.3 g (0.01 mole) of N'-(4,6-dimethyl-pyrimidin-2-yl)-N''-isobutoxy-N''',N''''-bis-(2-methoxycarbonyl-benzenesulphonyl)-guanidine, 1.0 g (0.01 mole) of methanesulphonic acid and 15 ml of acetone is stirred at 20° C. for 24 hours. The product obtained as crystals is isolated by filtration with suction.

6.8 g (94% of theory) of N'-(4,6-dimethylpyrimidin-2-yl)-N''-isobutoxy-N''',N''''-bis-(2-methoxycarbonylbenzenesulphonyl)-guanidine methanesulphonate of melting point 85° C. are obtained.

The compounds of the formula (I) listed in the following Table 1 can be prepared by process (a) to (c) described in the preceding examples:

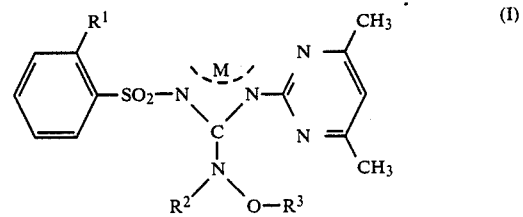

TABLE 1

| Example No. | $R^1$ | $R^2$ | $R^3$ | M | Melting Point (°C.) |
|---|---|---|---|---|---|
| 5 | Cl | 2-Cl-C$_6$H$_4$-SO$_2$- | -C$_4$H$_9$-n | H | 120 |
| 6 | -COOCH$_3$ | 2-(COOCH$_3$)-C$_6$H$_4$-SO$_2$- | -C$_4$H$_9$-n | H | 115 |
| 7 | -COOCH$_3$ | 2-(COOCH$_3$)-C$_6$H$_4$-SO$_2$- | -C$_8$H$_{17}$-n | H | 90 |
| 8 | -COOCH$_3$ | 2-(COOCH$_3$)-C$_6$H$_4$-SO$_2$- | -CH$_2$COOC$_2$H$_5$ | H | 134 |
| 9 | Cl | 2-Cl-C$_6$H$_4$-SO$_2$- | -CH$_2$COOC$_2$H$_5$ | H | 116 |
| 10 | -COOCH$_3$ | 2-(COOCH$_3$)-C$_6$H$_4$-SO$_2$- | -CH$_2$CH(CH$_3$)$_2$ | H | 147 |
| 11 | Cl | 2-Cl-C$_6$H$_4$-SO$_2$- | -CH(CH$_3$)CH$_2$CH$_3$ | H | 176 |
| 12 | -COOCH$_3$ | 2-(COOCH$_3$)-C$_6$H$_4$-SO$_2$- | -CH(CH$_3$)CH$_2$CH$_3$ | H | 113 |
| 13 | Cl | 2-Cl-C$_6$H$_4$-SO$_2$- | -CH$_2$CH(CH$_3$)$_2$ | H | 131 |
| 14 | -COOCH$_3$ | 2-(COOCH$_3$)-C$_6$H$_4$-SO$_2$- | -CH$_2$CH=CH$_2$ | H | 102 |
| 15 | -COOCH$_3$ | 2-(COOCH$_3$)-C$_6$H$_4$-SO$_2$- | -CH$_2$CH$_2$CH$_3$ | Na | 165 |

TABLE 1-continued

| Example No. | R¹ | R² | R³ | M | Melting Point (°C.) |
|---|---|---|---|---|---|
| 16 | —COOCH₃ | 2-(COOCH₃)-C₆H₄—SO₂— | —CH₂CH₂CH₃ | ½ Ca | 60 |
| 17 | Cl | 2-Cl-C₆H₄—SO₂— | —CH₂—(2-Cl-C₆H₄) | H | semi-crystalline oil |
| 18 | Cl | H | —CH₂COOCH₃ | H | 124 |
| 19 | Cl | H | —CH₂COOC₂H₅ | H | 110 |
| 20 | Cl | H | —CH₂COOCH(CH₃)₂ | H | 113 |
| 21 | Cl | H | —CH(CH₃)COOCH₃ | H | 125 |
| 22 | Cl | H | —CH(CH₃)COOC₂H₅ | H | 129 |
| 23 | —COOCH₃ | H | —CH₂COOH | H | 140 |
| 24 | —COOCH₃ | H | —CH₂COOCH₃ | H | 102 |
| 25 | —COOCH₃ | H | —CH₂COOC₂H₅ | H | 139 |
| 26 | —COOCH₃ | H | —CH₂COOCH(CH₃)₂ | H | 83 |
| 27 | —COOCH₃ | H | —CH(CH₃)COOCH₃ | H | 100 |
| 28 | —COOCH₃ | H | —CH(CH₃)COOC₂H₅ | H | 56 |
| 29 | Cl | 2-Cl-C₆H₄—SO₂— | —CH₂CH₂—C₆H₅ | H | 190 |
| 30 | —COOCH₃ | 2-(COOCH₃)-C₆H₄—SO₂— | —CH₂CH₂—C₆H₅ | H | 141 |
| 31 | —CH₂Cl | 2-(CH₂Cl)-C₆H₄—SO₂— | —CH₂—CH(CH₃)₂ | H | 149 |
| 32 | —CH₂Cl | 2-(CH₂Cl)-C₆H₄—SO₂— | —CH(CH₃)—C₂H₅ | H | 159 |
| 33 | —COOCH₃ | H | —CH₂—CH(CH₃)₂ | H | 110 |
| 34 | —COOCH₃ | H | —CH(CH₃)—C₂H₅ | H | 105 |

TABLE 1-continued
| Example No. | R¹ | R² | R³ | M | Melting Point (°C.) |
|---|---|---|---|---|---|
| 35 | Cl | H | 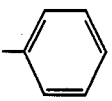 | H | 146–149 |
| 36 | —COOCH₃ | H | 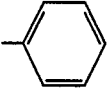 | H | 143–145 |
| 37 | —COOCH₃ | 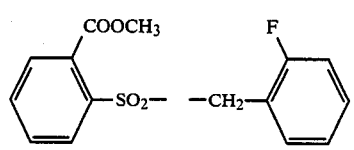 |  | H | (amorphous) |
| 38 | —COOCH₃ | 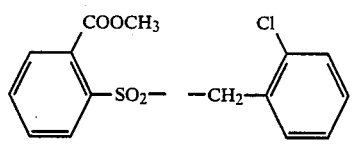 |  | H | (amorphous) |
| 39 | —COOCH₃ | 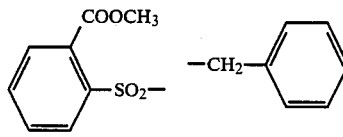 | 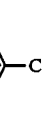 | H | 70–71 |
| 40 | —COOCH₃ | 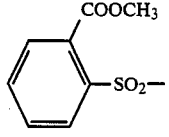 | —CH(CH₃)₂ | H | 109 |
| 41 | —COOCH₃ | H | 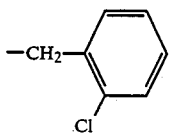 | H | amorphous |
| 42 | —Cl | 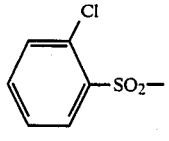 | 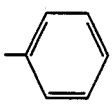 | H | 135–37 |
| 43 | —Cl | 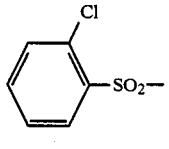 | —CH(CH₃)₂ | H | 185 |
| 44 | —COOCH₃ | H | —CH₂CH₂CH₂Cl | H | 111 |
| 45 | —Cl | 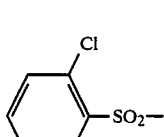 |  | H | 185 |

TABLE 1-continued

| Example No. | R¹ | R² | R³ | M | Melting Point (°C.) |
|---|---|---|---|---|---|
| 46 | —COOCH₃ | ![COOCH₃ phenyl SO₂—] (2-COOCH₃-C₆H₄-SO₂—) | —CH₂-(2,6-dichlorophenyl) | H | 170 |
| 47 | —COOCH₃ | H | —CH₂-(4-NO₂-C₆H₄) | H | 155 |
| 48 | —COOCH₃ | H | —CH₂-(2,4-dinitrophenyl) | H | 137 |

The following acid adducts of compounds of the formula (I) were furthermore obtained analogously to process (d):

(12a) the 1:1 adduct of the product from Example (12) with methanesulphonic acid, of melting point 158° C., (12b) the 1:1 adduct of the product from Example (12) with sulphuric acid, of melting point 136° C.

(10a) the 1:1 adduct of the product from Example (10) with sulphuric acid, as a semi-solid mass.

(31a) the 1:1 adduct of the product from Example (31) with methanesulphonic acid of melting point 169° C.

(40a) the 1:1 adduct of the product from Example (40) with methanesulphonic acid of melting point 157° C.

(14a) the 1:1 adduct of the product from Example (14) with methanesulphonic acid, of melting point 126° C.

(14b) the 1:1 adduct of the product from Example (14) with sulphuric acid of melting point 119° C.

(44a) the 1:1 adduct of the product from Example (44) with sulphuric acid, of melting point 165° C.

(45) the 1:1 adduct of the product from Example (45) with p-toluenesulphonic acid, of melting point 167° C.

(46a) the 1:1 adduct of the product from Example (46) with p-toluenesulphonic acid, of melting point 160° C.

(46b) the 1:1 adduct of the product from Example (46) with methanesulphonic acid, of melting point 120° C.

STARTING SUBSTANCES OF THE FORMULA (II)

Example (II-1)

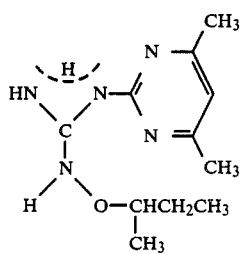

A mixture of 143 g (0.97 mole) of 2-cyanamino-4,6-dimethyl-pyrimidine, 94.3 g (1.06 moles) of O-sec.-butyl-hydroxylamine and 190 ml of ethanol is heated at the boiling point under reflux for 6 hours. The mixture is then filtered with suction, the filtrate is concentrated and 500 ml of water are added to the residue. The product thereby obtained as crystals is isolated by filtration with suction.

131 g (57% of theory) of N'-(4,6-dimethyl-pyrimidin-2-yl)-N''-sec.-butoxy-guanidine of melting point 78° C. are obtained.

The compounds of the formula (II) listed in the following Table 2 can be prepared analogously:

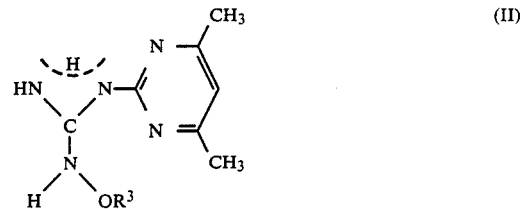

TABLE 2

| Example No. | R³ | Melting point (°C.) |
|---|---|---|
| II-2 | —CH₂CH(CH₃)₂ | 52 |
| II-3 | —CH₂CH=CH₂ | 103 |
| II-4 | —CH(CH₃)₂ | 84 |
| II-5 | —CH₂CH₂-C₆H₅ | $n_D^{24}$: 1.5776 |
| II-6 | —C₄H₉—n | (Oil) |
| II-7 | —C₈H₁₇—n | 58 |
| II-8 | —CH₂-(2-Cl-C₆H₄) | 102–103 |
| II-9 | —CH₂CH₂CH₂Cl | 137 |

TABLE 2-continued

| Example No. | R³ | Melting point (°C.) |
|---|---|---|
| II-10 | phenyl (—C₆H₅) | 192 (decomposition) |
| II-11 | —CH₂—COOCH₃ | 148–149 |
| II-12 | —CH₂—COOC₂H₅ | 98–99 |
| II-13 | —CH(CH₃)—COOCH₃ | 147–148 |
| II-14 | —CH₂—(4-CH₃-C₆H₄) | 85–86 |
| II-15 | —CH₂—(2-F-C₆H₄) | 114 |
| II-16 | cyclohexyl | |
| II-17 | —CH₂—cyclohexyl | |
| II-18 | —CH₂CON(CH₃)₂ | |
| II-19 | —CH₂OCH₃ | |
| II-20 | —CH₂SCH₃ | |
| II-21 | —CH₂CF₃ | |
| II-22 | —CH₂—(2,6-Cl₂-C₆H₃) | 145 |
| II-23 | —CH₂—(4-COOC₂H₅-C₆H₄) | 138 |
| II-24 | —CH₂—(4-NO₂-C₆H₄) | 172 |
| II-25 | —CH₂—CH₂—CH₃ | (oil) |
| II-26 | —CH₂—COOC₃H₇(—i) | 112 |
| II-27 | —CH(C₆H₅)₂ | |

Example A

Pre-emergence test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0% = no action (like untreated control)
100% = total destruction

In this test, the active compounds according to the invention exhibit a very good herbicidal activity. This particularly applies, for example, to the compounds according to preparation Examples 3, 4, 5, 6, 7, 10, 12, 40.

Example B

Post-emergence test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Test plants which have a height of 5–15 cm are sprayed with the preparation of the active compound in such a way as to apply the particular amounts of active compound desired per unit area. The concentration of the spray liquor is so chosen that the particular amounts of active compound desired are applied in 2,000 l of water/ha. After three weeks, the degree of dosage to the plants is rated in % damage in comparison to the development of the untreated control. The figures denote:

0% = no action (like untreated control)
100% = total destruction

In this test, the active compounds according to the invention exhibit very good herbicidal activity. This particularly applies, for example, to the compounds according to preparation Examples 1, 3, 4, 5, 6, 7, 10, 12, 14, 40.

It will be understood that the specification and examples are illustrative but not limitative of the present invention and that other embodiments within the spirit and scope of the invention will suggest themselves to those skilled in the art.

We claim:

1. An oxyguanidine derivative of the formula

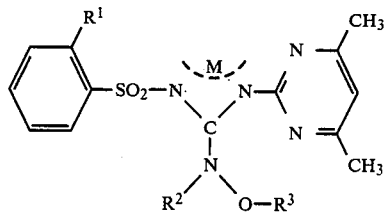

in which

M represents hydrogen or one equivalent of a metal,

R¹ represents halogen, $C_1$–$C_4$-alkyl, $C_1$–$C_2$-halogenoalkyl, $C_1$–$C_4$-alkoxy, phenyl or $C_1$–$C_2$-alkoxy-carbonyl, R² represents hydrogen or the radical

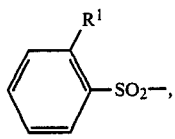

and

R³ represents $C_4$–$C_{12}$-alkyl, isopropyl or—if M represents one equivalent of a metal—also propyl, or represents $C_2$–$C_{12}$-halogenoalkyl, $C_1$–$C_4$-alkoxycarbonyl-$C_1$–$C_2$-alkyl, aminocarbonylmethyl, $C_1$–$C_4$-alkylaminocarbonylmethyl, di-$C_1$–$C_4$-alkylaminocarbonylmethyl, $C_3$–$C_{12}$-alkenyl, $C_3$–$C_{12}$-alkinyl, benzyl which is substituted by halogen, nitro, cyano, $C_1$–$C_4$-alkyl, $C_1$–$C_4$-alkoxy or $C_1$–$C_4$-alkoxycarbonyl, or phenyl, benzhydryl, or phenethyl, all optionally substituted by halogen, nitro, cyano, $C_1$–$C_4$-alkyl, $C_1$–$C_4$-alkoxy or $C_1$–$C_4$-alkoxycarbonyl, or carboxy-$C_1$–$C_2$-alkyl, or an adduct thereof with a strong acid.

2. A compound, salt or adduct according to claim 1, in which

M represents hydrogen or one equivalent of sodium, potassium or calcium,

R¹ represents fluorine, chlorine, bromine, methyl, chloromethyl, trifluoromethyl, methoxy, phenyl or methoxycarbonyl or ethoxycarbonyl, R² represents hydrogen or the radical

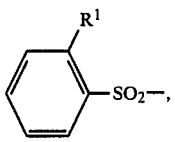

and

R³ represents $C_4$–$C_8$-alkyl, isopropyl or—in the case where M represents one equivalent of a metal—also propyl, or represents $C_2$–$C_8$-halogenoalkyl, $C_1$–$C_2$-alkoxycarbonyl-$C_1$–$C_2$-alkyl, aminocarbonylmethyl, $C_1$–$C_3$-alkylaminocarbonylmethyl, di-$C_1$–$C_3$-alkylaminocarbonylmethyl, $C_3$–$C_8$-alkenyl, $C_3$–$C_8$-alkinyl, benzyl which is substituted by fluorine, chlorine, nitro, cyano, methyl, methoxy or $C_1$–$C_2$-alkoxy-carbonyl, or phenyl, benzhydryl, or phenethyl, all three optionally substituted by fluorine, chlorine, nitro, cyano, methyl, methoxy or $C_1$–$C_2$-alkoxycarbonyl.

3. A compound, salt or adduct according to claim 1, in which

R¹ represents fluorine, chlorine, bromine, chloromethyl or methoxycarbonyl,

R² represents the radical

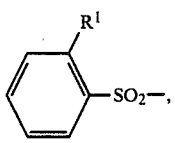

and

R³ represents $C_4$–$C_8$-alkyl, isopropyl or—in the case where M represents one equivalent of a metal—also propyl, or $C_2$–$C_4$-halogenoalkyl, $C_1$–$C_2$-alkoxycarbonyl-$C_1$–$C_2$-alkyl, aminocarbonylmethyl, $C_3$–$C_5$-alkenyl, $C_3$–$C_5$-alkinyl, benzyl which is substituted by fluorine, chlorine, nitro, methyl or $C_1$–$C_2$-alkoxycarbonyl, or phenyl or phenethyl, optionally substituted by fluorine, chlorine, nitro, methyl or $C_1$–$C_2$-alkoxycarbonyl.

4. A compound according to claim 1, wherein such compound is N'-(4,6-dimethylpyrimidin-2-yl)-N''-octyloxy-N'',N'''-bis-(2-chlorobenzene-sulphonyl)-guanidine of the formula

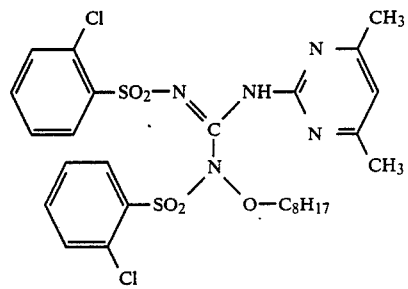

or a sodium, potassium or calcium salt thereof or an adduct thereof with a strong acid.

5. A compound according to claim 1, wherein such compound is N'-(4,6-dimethylpyrimidin-2-yl)-N''-propoxy-N'',N'''-bis-(2-methoxy-carbonyl-benzenesulphonyl)-guanidine of the formula

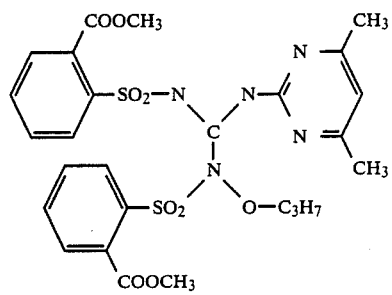

or a sodium, potassium or calcium salt thereof or an adduct thereof with a strong acid.

6. A compound according to claim 1, wherein such compound is N'-(4,6-dimethylpyrimidin-2-yl)-N''-isobutoxy-N'',N'''-bis-(2-methoxycarbonyl-benzenesulphonyl)-guanidine of the formula

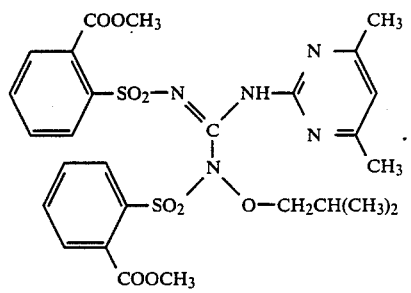

or a sodium, potassium or calcium salt thereof or an adduct thereof with a strong acid.

7. A compound according to claim 1, wherein such compound is N'-(4,6-dimethylpyrimidin-2-yl)-N''-butoxy-N'',N'''-bis-(2-chlorobenzene-sulphonyl)-guanidine of the formula

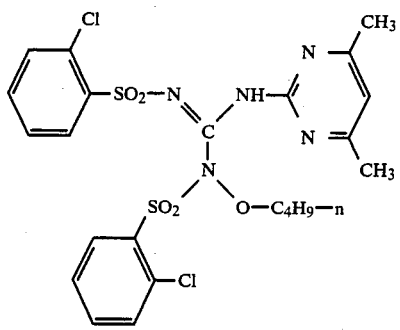

or a sodium, potassium or calcium salt thereof or an adduct thereof with a strong acid.

8. A compound according to claim 1, wherein such compound is N'-(4,6-dimethylpyrimidin-2-yl)-N''-butoxy-N'',N'''-bis-(2-methoxycarbonyl-benzenesulphonyl)-guanidine of the formula

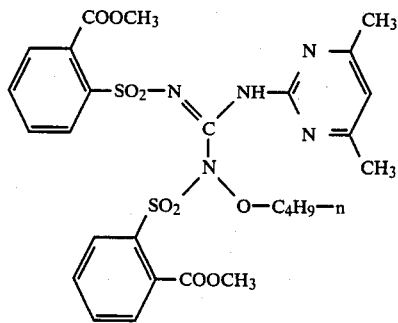

or a sodium, potassium or calcium salt thereof or an adduct thereof with a strong acid.

9. A compound according to claim 1, wherein such compound is N'-(4,6-dimethylpyrimidin-2-yl)-N''-octyloxy-N'',N'''-bis-(2-methoxycarbonyl-benzenesulphonyl)-guanidine of the formula

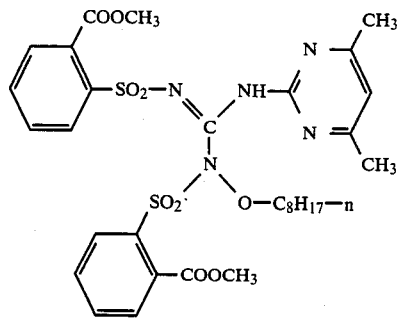

or a sodium, potassium or calcium salt thereof or an adduct thereof with a strong acid.

10. A compound according to claim 1, wherein such compound is N'-(4,6-dimethylpyrimidin-2-yl)-N''-sec.-butoxy-N'',N'''-bis-(2-methoxycarbonyl-benzenesulphonyl)-guanidine of the formula

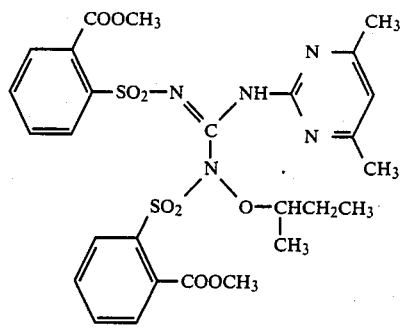

or a sodium, potassium or calcium salt thereof or an adduct thereof with a strong acid.

11. A compound according to claim 1, wherein such compound is N'-(4,6-dimethylpyrimidin-2-yl)-N''-allyloxy-N'',N'''-bis-(2-methoxycarbonyl-benzenesulphonyl)-guanidine of the formula

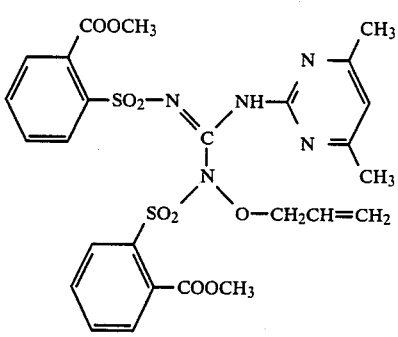

or a sodium, potassium or calcium salt thereof or an adduct thereof with a strong acid.

12. A compound according to claim 1, wherein such compound is N'-(4,6-dimethylpyrimidin-2-yl)-N''-isopropoxy-N'',N'''-bis-(2-methoxycarbonyl-benzenesulphonyl)-guanidine of the formula

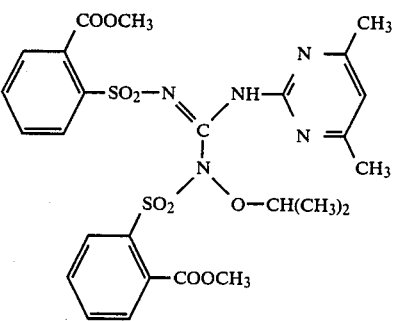

or a sodium, potassium or calcium salt thereof or an adduct thereof with a strong acid.

13. A herbicidal composition comprising a herbicidally effective amount of a compound, salt or adduct according to claim 1 in admixture with a diluent.

14. A method of combating unwanted vegetation which comprises applying to such vegetation or to a locus from which it is desired to exclude such vegetation a herbicidally effective amount of a compound, salt or adduct according to claim 1.

15. The method according to claim 1, wherein such compound is

N'-(4,6-dimethylpyrimidin-2-yl)-N'''-octyloxy-N'',N'''-bis-(2-chlorobenzene-sulphonyl)-guanidine, N'-(4,6-dimethylpyrimidin-2-yl)-N'''-propoxy-N'',N'''-bis-(2-methoxy-carbonyl-benzenesulphonyl)-guanidine, N'-(4,6-dimethylpyrimidin-2-yl)-N'''-isobutoxy-N'',N'''-bis-(2-methoxycarbonyl-benzenesulphonyl)-guanidine, N'-(4,6-dimethylpyrimidin-2-yl)-N'''-butoxy-N'',N'''-bis-(2-chlorobenzene-sulphonyl)-guanidine, N'-(4,6-dimethylpyrimidin-2-yl)-N'''-butoxy-N'',N'''-bis-(2-methoxycarbonyl-benzenesulphonyl)-guanidine, N'-(4,6-dimethylpyrimidin-2-yl)-N'''-octyloxy-N'',N'''-bis-(2-methoxycarbonyl-benzenesulphonyl)-guanidine, N'-(4,6-dimethylpyrimidin-2-yl)-N'''-sec.-butoxy-N'',N'''-bis-(2-methoxycarbonyl-benzenesulphonyl)-guanidine, N'-(4,6-dimethylpyrimidin-2-yl)-N'''-allyloxy-N'',N'''-bis-(2-methoxyearbonyl-benzenesulphonyl)-guanidine or N'-(4,6-dimethylpyrimidin-2-yl)-N'''-isopropoxy-N'',N'''-bis-(2-methoxycarbonyl-benzenesulphonyl)-guanidine, or a sodium, potassium or calcium salt thereof or an adduct thereof with a strong acid.

* * * * *